United States Patent [19]

Levitt

[11] 4,454,335

[45] Jun. 12, 1984

[54] SUBSTITUTED BENZENE SULFONYL ISOCYANATES AS INTERMEDIATES TO HERBICIDAL SULFONAMIDES

[75] Inventor: George Levitt, Wilmington, Del.

[73] Assignee: E. I. Du Pont de Nemours and Company, Wilmington, Del.

[21] Appl. No.: 378,397

[22] Filed: Jun. 14, 1982

Related U.S. Application Data

[60] Division of Ser. No. 254,256, Apr. 29, 1981, Pat. No. 4,348,219, which is a continuation-in-part of Ser. No. 168,348, Jul. 11, 1980, abandoned.

[51] Int. Cl.$^3$ .......................................... C07C 143/828
[52] U.S. Cl. ........................................................ 560/12
[58] Field of Search ............................ 560/12; 562/430

[56] References Cited

U.S. PATENT DOCUMENTS 4,293,701 10/1981 Pallos et al. ............................ 560/12

*Primary Examiner*—Paul M. Coughlan, Jr.

[57] ABSTRACT

Novel o-aminosulfonylphenyl acetic acid derivatives are useful as plant growth regulants and herbicides.

1 Claim, No Drawings

SUBSTITUTED BENZENE SULFONYL ISOCYANATES AS INTERMEDIATES TO HERBICIDAL SULFONAMIDES

RELATED APPLICATION

This is a division of application Ser. No. 254,256, filed Apr. 29, 1981, U.S. Pat. No. 4,348,219, which is a continuation-in-part of application Ser. No. 168,348 filed July 11, 1980, now abandoned.

BACKGROUND OF THE INVENTION

This invention relates to o-aminosulfonylphenyl acetic acid derivatives which are useful as plant growth regulants and herbicides.

French Pat. No. 1,468,747 discloses the following para-substituted phenylsulfonamides, useful as antidiabetic agents:

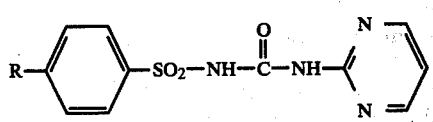

where R=H, halogen, $CF_3$ or alkyl.

Logemann et al., Chem. Ab., 53, 18052 g (1959), disclose a number of sulfonamides, including uracil derivatives and those having the formula:

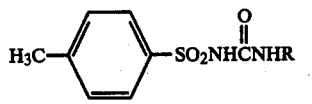

wherein R is butyl, phenyl or

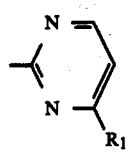

and $R_1$ is hydrogen or methyl. When tested for hypoglycemic effect in rats (oral doses of 25 mg/100 g), the compounds in which R is butyl or phenyl were most potent. The others were of low potency or inactive.

Wojciechowski, J. Acta. Polon. Pharm. 19, P. 121-5 (1962) [Chem. Ab., 59 1633 e] describes the synthesis of N-[(2,6-dimethoxypyrimidin-4-yl)aminocarbonyl]-4-methylbenzenesulfonamide:

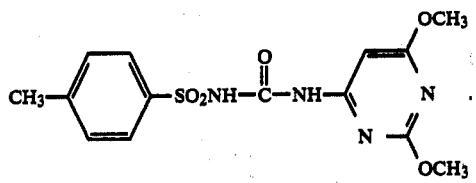

In U.S. Pat. No. 4,127,405, the following compounds are taught to have herbicidal activity:

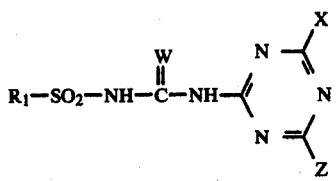

wherein

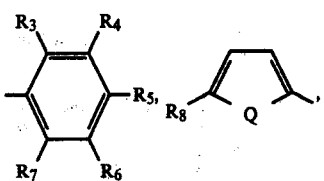

$R_1$ is

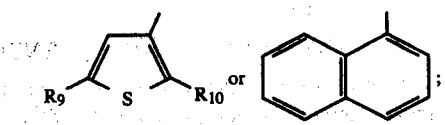

$R_3$ and $R_6$ are independently hydrogen, fluorine chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Z is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In particular, the patent discloses orthosubstituted compounds wherein the substitution is $C_1$-$C_4$ alkyl.

The presence of undesired vegetation causes substantial damage to useful crops, especially agricultural products that satisfy man's basic food needs, such as soybeans, corn, wheat and the like. The current population explosion and concomitant world food shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for effective herbicides that destroy or control weeds while not significantly damaging useful crops.

J. Heterocyclic Chemistry, 8, 947 (1971) discloses:

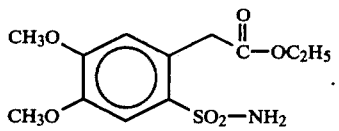

Chemische Berichte, 103, 1992 (1970) discloses:

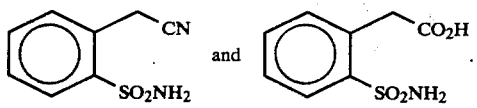

SUMMARY OF THE INVENTION

This invention relates to novel compounds of Formula I and their agriculturally suitable salts, suitable agricultural compositions containing them, and their method of use as general and selective pre-emergence and post-emergence herbicides and as plant growth regulants.

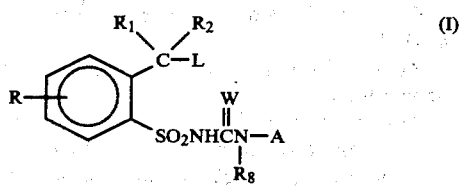

wherein

L is $CO_2R_{10}$, $CONR_3R_4$ or CN;

R is H, F, Cl, Br, $NO_2$, $CF_3$, $C_1$-$C_3$ alkyl or $C_1$-$C_3$ alkoxy;

$R_1$ is H or $C_1$-$C_4$ alkyl;

$R_2$ is H or $CH_3$;

$R_3$ is H, $C_1$-$C_4$ alkyl or $OCH_3$;

$R_4$ is H or $C_1$-$C_4$ alkyl;

$R_3$ and $R_4$ can be taken together to form —$(CH_2)_4$—, —$(CH_2)_5$— or —$(CH_2CH_2)_2O$;

$R_8$ is H, $CH_3$ or $OCH_3$;

$R_{10}$ is H, $C_1$-$C_4$ alkyl, $C_3$-$C_4$ alkenyl, $CH_2CH_2Cl$ or $CH_2CH_2OCH_3$;

A is

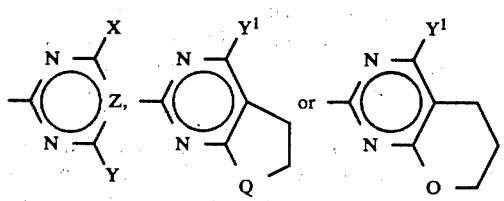

W is O or S;

X is H, Cl, Br, $CH_3$, $CH_2CH_3$, $C_1$-$C_3$ alkoxy, $CF_3$, $SCH_3$ or $CH_2OCH_3$;

Y is $CH_3$ or $OCH_3$;

Z is N, CH, CCl, CBr, CCN, $CCH_3$, $CCH_2CH_3$, $CCH_2CH_2Cl$ or $CCH_2CH=CH_2$;

$Y^1$ is H, $CH_3$, $OCH_3$ or $OCH_2CH_3$; and

Q is O or $CH_2$;

and their agriculturally suitable salts; provided that:

(1) when L is $CONR_3R_4$, then Z is CH or N;

(2) when $R_3$ is $OCH_3$, then $R_4$ is $CH_3$; and (3) when W is S, $R_8$ is H.

Preferred in increasing order for their higher activity and/or more favorable ease of synthesis are:

(1) Compounds of the generic scope wherein L is $CO_2R_{10}$, W is O, Z is N, CH, CCl, CBr or $CCH_3$, and $R_8$ is H or $CH_3$;

(2) Compounds of Preferred (1) wherein Z is CH or N, X is $CH_3$ or $OCH_3$, and $R_1$ and $R_2$ are H;

(3) Compounds of Preferred (2) wherein A is

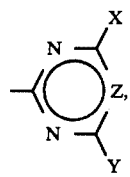

$R_8$ is H and R is H;

(4) Compounds of Preferred (3) wherein $R_{10}$ is $CH_3$ or $CH_2CH_3$.

Specifically Preferred for highest activity and/or most favorable ease of synthesis are:

2-[[(4,6-dimethoxypyrimidin-2-yl)aminocarbonyl]aminosulfonyl]benzeneacetic acid, methyl ester;

2-[[(4,6-dimethylpyrimidin-2-yl)aminocarbonyl]aminosulfonyl]benzeneacetic acid, methyl ester;

2-[[(4-methoxy-6-methylpyrimidin-2-yl)aminocarbonyl]aminosulfonyl]benzeneacetic acid, methyl ester;

2-[[(4,6-dimethoxy-1,3,5-triazin-2-yl)aminocarbonyl]aminosulfonyl]benzeneacetic acid, methyl ester;

2-[[(4-methoxy-6-methyl-1,3,5-triazin-2-yl)aminocarbonyl]aminosulfonyl]benzeneacetic acid, methyl ester;

2-[[(4,6-dimethoxypyrimidin-2-yl)aminocarbonyl]aminosulfonyl]benzeneacetic acid, ethyl ester; and 2-[[(4-methoxy-6-methylpyrimidin-2-yl)aminocarbonyl]aminosulfonyl]benzeneacetic acid, ethyl ester.

This invention also relates to novel compounds of Formula II which are useful intermediates for the preparation of the herbicidal compounds of Formula I.

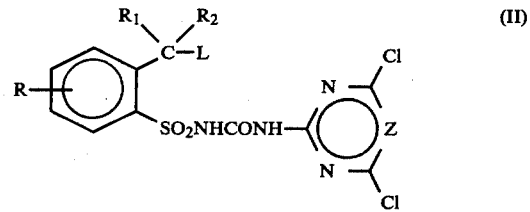

wherein L, R, $R_1$, and $R_2$ are as previously defined, and Z is CH or N; provided that when $R_3$ is $OCH_3$, then $R_4$ is $CH_3$, and that $R_{10}$ cannot be H.

This invention also relates to novel compounds of Formula III which are useful intermediates for the preparation of the compounds of Formula I:

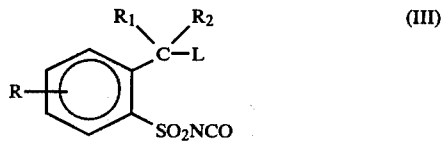

wherein
L is $CO_2R_{10}$;
R, $R_1$, $R_2$ and $R_{10}$ are as previously defined;
provided that $R_{10}$ cannot be H.

DETAILED DESCRIPTION OF THE INVENTION

Synthesis

As shown in Equation 1, the compounds of Formula I can be prepared by combining an appropriately substituted 2-aminoheterocycle of Formula IV with an appropriately substituted sulfonyl isocyanate of Formula III; R, $R_1$, $R_2$, $R_8$ and A are as previously defined, and L is $CO_2R_{10}$, provided that $R_{10}$ cannot be H.

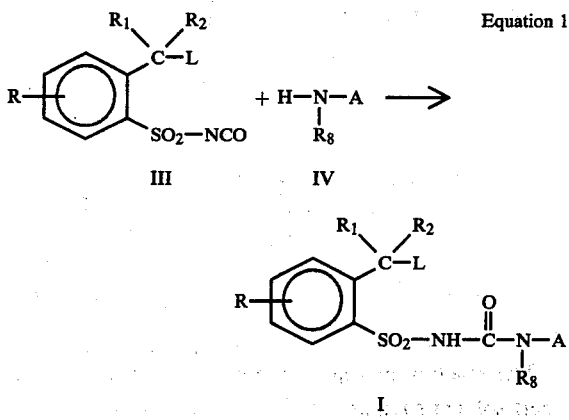

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminoheterocycle. Since the isocyanates often are liquids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether or pentane and filtration.

The intermediate sulfonyl isocyanates of Formula III in which L is $CO_2R_{10}$, provided that $R_{10}$ cannot be H, are also novel compounds and can be prepared by reacting the corresponding sulfonamides (V) with phosgene in the presence of an alkyl isocyanate such as butyl or cyclohexyl isocyanate at reflux in a solvent such as chlorobenzene, according to the procedure of H. Ulrich and A. A. Y. Sayigh, *Newer Methods of Preparative Organic Chemistry*, Vol. VI, p. 223-241, Academic Press, New York and London, W. Foerst, Ed. In cases where formation of the desired sulfonyl isocyanate is difficult by the above procedure, the preformed sulfonylurea from the reaction of butyl isocyanate with the appropriate sulfonamide is treated with phosgene according to the above reference.

Alternatively, the process of Ulrich and Sayigh can be varied by the addition of a tertiary base to the reaction mixture as shown by Equation 2 in which L is $CO_2R_{10}$, provided that $R_{10}$ cannot be H.

A mixture of the appropriate benzenesulfonamide (V), an alkyl isocyanate such as butyl isocyanate and a catalytic amount of 1,4-diaza[2,2,2]bicyclooctane (DABCO) in xylene or other inert solvent of sufficiently high boiling point (e.g. >135°) is heated to approximately 135°. Phosgene is added to the mixture until an excess is present as indicated by a drop in the boiling point. The mixture is heated further to drive off the excess phosgene. After the mixture is cooled and filtered to remove a small amount of insoluble by-products, the solvent and alkyl isocyanate are distilled off in vacuo leaving a residue which is the crude sulfonyl isocyanate (III).

The preparation of sulfonamides from ammonium hydroxide and sulfonyl chlorides is widely reported in the literature, e.g., Crossely et al., *J. Am. Chem. Soc.* 60, 2223 (1938).

Certain sulfonyl chlorides are best prepared by chlorosulfonation of a substituted benzene according to the teaching of H. T. Clarke et al. *Org. Synth.* Coll. Vol. 1, 2nd Ed. 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.*, 25, 1824 (1960).

The synthesis of heterocyclic amine derivatives has been reviewed in "The Chemistry of Heterocyclic Compounds", a series published by Interscience Publ., New York and London. 2-Aminopyrimidines are described by D. J. Brown in "The Pyrimidines", Vol. XVI of the above series.

2-Amino-1,3,5-triazines can be synthesized according to the methods described by E. M. Smolin and L. Rapaport in "s-Triazines and Derivatives", Vol. XIII of the same series.

The preparation of fused ring pyrimidine amines are disclosed in various publications, such as: Braken et al., *J. Am. Chem. Soc.*, 69, 3072 (1947); Mitten and Bharlacharya, *Quart. J. Ind. Chem. Soc.* 4, 152 (1927), Schrage and Hitchings, *J. Org. Chem.*, 16, 1153 (1951); Svab et al., *Coll. Czech Commun.* 32, 1582 (1967).

Compounds of Formula IX are prepared by the reaction of about two equivalents of aqueous sodium hydroxide with the compounds of Formula I in which $R_{10}$ is $C_1$-$C_4$, preferably methyl (VIII), followed by acidification of the solution. This process is illustrated in Equation 3, wherein R, $R_1$, $R_2$, $R_8$ and A are as previously defined.

Equation 3

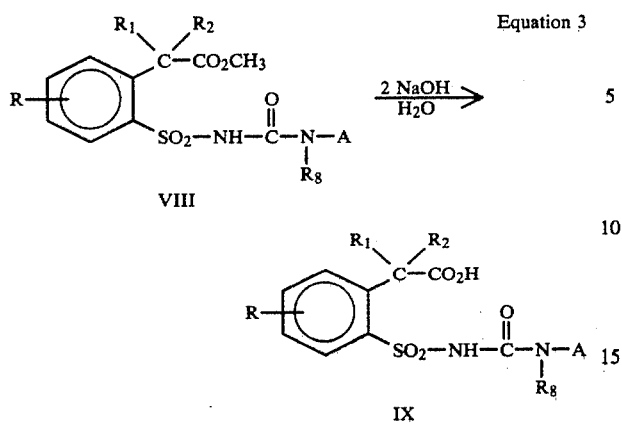

The reaction is carried out over the course of 2-6 hours in water, by stirring the compound of Formula VIII with two equivalents of sodium hydroxide or potassium hydroxide at ambient temperature. The aqueous solution is then acidified with hydrochloric or sulfuric acid, which causes the compound of Formula IX to precipitate out. It is then isolated by filtration.

Compounds of Formula X are prepared by reacting an appropriately substituted compound of Formula I in which $R_{10}$ is $C_1-C_4$ alkyl, preferably methyl (VIII), with a dialkylaluminum-N-alkylamide derivative, as shown in Equation 4, wherein R, $R_1$, $R_2$, $R_3$, $R_4$, $R_8$ and A are as previously defined.

Equation 4

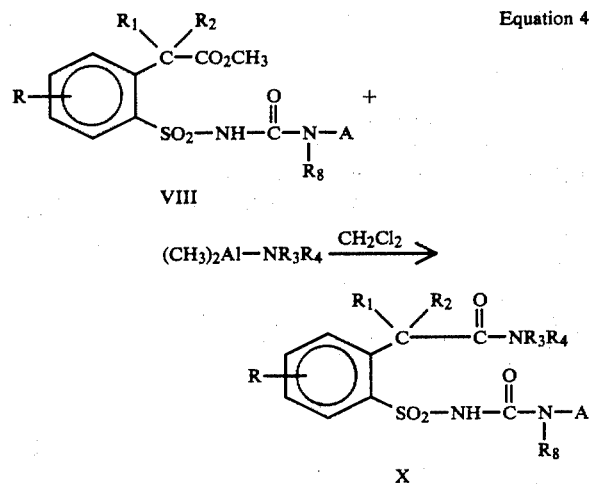

The intermediate alkylaminoaluminum compounds are prepared according to A. Basha, M. Lipton and S. W. Weinreb, *Tetrahedron Letters*, 4171 (1977) by reacting the trialkylaluminum, preferably trimethylaluminum, and the corresponding amine. The $(CH_3)_2Al-NR_3R_4$ intermediate is co-mingled with a suspension of the compound of Formula VIII in an inert solvent, preferably methylene chloride, and the mixture is refluxed for one to twenty-four hours. The product is isolated by adding aqueous hydrochloric acid to decompose the resulting complex, and then evaporating the methylene chloride phase. The desired product can be further purified by recrystallization of column chromatography.

Compounds of Formula XIII can be prepared by reacting an appropriately substituted sulfonamide of Formula XI with the methylcarbamate of the appropriate aminoheterocycle (XII) in the presence of an equivalent amount of trimethylaluminum, as shown in Equation 5, wherein R, $R_1$, $R_2$, $R_8$ and A are as previously defined.

Equation 5

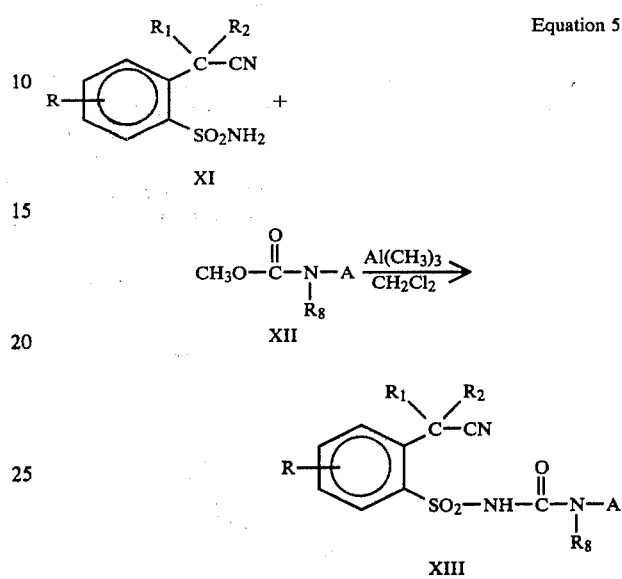

The reaction of Equation 5 is best carried out in an inert solvent such as methylene chloride at 10°-45° C. and atmospheric pressure. The preferred mode of addition is to add the triethylaluminum to a solution or slurry of the sulfonamide (XI); a mildly exothermic reaction occurs accompanied by the evolution of gas. The addition of the heterocyclic carbamate (XII) is then made and the mixture is stirred at ambient to reflux temperature for 6 to 48 hours. The addition of aqueous acid such as dilute hydrochloric or acetic acid removes organic salts from the product contained in the organic phase. Evaporation of the methylene chloride yields the crude product, which can be purified by recrystallization or column chromatography.

Some of the compounds of Formula I can also be prepared by the method shown in Equation 6, using the novel intermediates of Formula II, wherein L, R, $R_1$, $R_2$, $R_3$, $R_4$ and $R_{10}$ are as previously defined, and wherein Z is CH or N, and $R_{12}$ is $C_1-C_3$ alkyl.

Equation 6

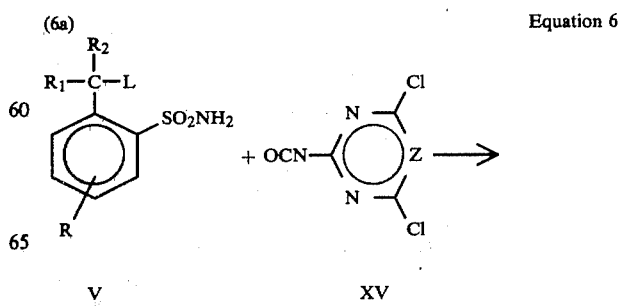

-continued

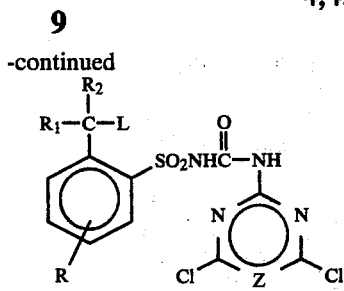

II

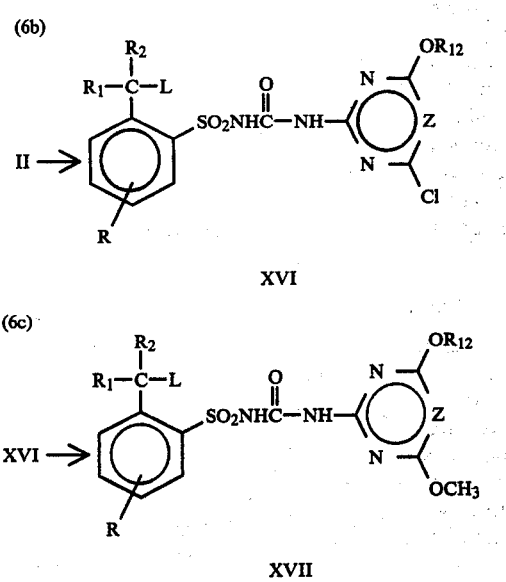

Reaction Step (6a)

In Reaction Step (6a), an aromatic sulfonamide of Formula V is contacted with a heterocyclic isocyanate of Formula XV to yield an N-(haloheterocyclicaminocarbonyl)aromatic sulfonamide of Formula II.

The heterocyclic isocyanates used in Reaction (6a) may be prepared according to methods described in Swiss Pat. No. 579,062, U.S. Pat. No. 3,919,228, U.S. Pat. No. 3,732,223 and Angew Chem. Int. Ed. 10, 402 (1976), the disclosures of which are herein incorporated by reference.

The aromatic sulfonamide and the heterocyclic isocyanate are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110°, and the product can generally be recovered by cooling and filtering the reaction mixture. For reasons of efficiency and economy, the preferred solvents are acetonitrile and THF, and the preferred temperature range is about 60° to 85° C.

Reaction Steps (6b) and (6c)

In Reaction Steps (6b) and (6c), one or two of the halogen atoms on the heterocyclic ring of the compound of Formula II is displaced by a nucleophilic species. Generally this may be done by contacting the compound of Formula II either with alkanol, $R_{12}OH$ or with alkoxide, $-OR_{12}$, where $R_{12}$ is as defined above.

Thus, in Reaction Step (6b), a compound of Formula II can be contacted with at least one equivalent of alkanol, $R_{12}OH$. This reaction is sluggish, however, and it is preferred to contact the compound of Formula II with at least two equivalents of alkoxide, $OR_{12}$. The alkoxide can be provided in a number of ways:

(a) The compound of Formula II can be suspended or dissolved in an alkanol solvent, $R_{12}OH$, in the presence of at least two equivalents of alkoxide, $OR_{12}$. The alkoxide can be added directly as alkali metal or alkaline earth metal alkoxide or can be generated by the addition to the alkanol solvent of at least two equivalents of a base capable of generating alkoxide from the solvent. Suitable bases include but are not limited to, the alkali and alkaline earth metals, their hydrides and tert-butoxides. For example, when $R_{12}$ is methyl, the compound of Formula II could be suspended or dissolved in methanol in the presence of two equivalents of sodium methoxide. Alternatively, two equivalents of sodium hydride could be used in place of the sodium methoxide.

(b) The compound of Formula II can be suspended or dissolved in an inert solvent in the presence of at least two equivalents of alkoxide, $OR_{12}$. Suitable inert solvents include, but are not limited to, acetonitrile, THF and dimethylformamide. The alkoxide may be added directly as alkali metal or alkaline earth metal alkoxide or may be generated from alkanol and a base as described in (a) above. For example, when $R_{12}$ is methyl, the compound of Formula II could be suspended or dissolved in THF in the presence of two equivalents of sodium methoxide. Alternatively, two equivalents each of methanol and sodium hydride could be used instead of sodium methoxide.

For reasons of economy and efficiency, procedure (a) is the more preferred method.

It should be noted that two equivalents of alkoxide are required for Reaction Step (6b) whereas only one equivalent of alkanol is needed for the same process. This difference is due to the reaction which is believed to occur between the alkoxide and the sulfonyl nitrogen of the sulfonamide of Formula II. When alkoxide is used, the first equivalent of alkoxide removes a proton from the sulfonyl nitrogen, and it is only the second equivalent which effects displacement of the halogen. As a result, two equivalents of alkoxide are required. The resulting salt must be acidified, e.g., with sulfuric, hydrochloric or acetic acid, to yield a compound of Formula XVI. Applicant, of course, does not intend to be bound by the mechanism described above.

In Reaction Step (6c), a compound of Formula XVI is contacted with either one equivalent of methanol, or with two equivalents of methoxide, $-OCH_3$. When methoxide is used, it may be provided in either of the methods described above in connection with Reaction Step (6b), and the resulting salt can be acidified to yield a compound of Formula XVII.

When $R_{12}=CH_3$, Reaction Steps (6b) and (6c) may be combined. Thus, a compound of Formula II may be contacted either with at least two equivalents of methanol or with at least three equivalents of methoxide.

For a compound of Formula II, certain reaction conditions will favor displacement of only one of the chlorines. These conditions are the use of low temperatures and, when alkoxide is used, the slow addition of the stoichiometric amount of alkoxide or alkoxide-generating base to the medium containing the compound of Formula II.

When alkoxide is used, both Reaction Steps (6b) and (6c) are preferably run at temperatures within the range of about −10° to 80° C., the range of about 0° to 25° C. being more preferred. Reaction Steps (6b) and (6c) are more sluggish when alkanol is used instead of alkoxide, and more drastic conditions are required for the reaction to go to completion. Thus, higher temperatures, up to and including the boiling point of the alkanol itself, are required.

As shown in Equation 7, compounds of Formula XIX, in which R, $R_1$, $R_2$, L and A are as previously defined, are prepared by the reaction of an appropriately substituted sulfonamide, (V), with a heterocyclic isothiocyanate of Formula XVIII.

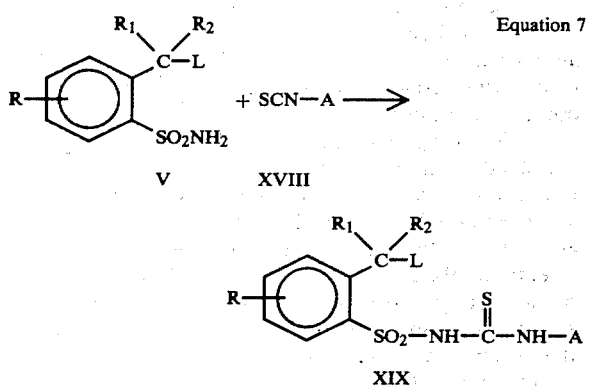

Equation 7

The Reaction of Equation 7 is best carried out by dissolving or suspending the sulfonamide and isothiocyanate in a polar solvent such as acetone, acetonitrile, ethyl acetate or methyl ethyl ketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 7 are prepared, for example, according to the method of Japan Patent Application Pub: Kokai No. 51-143686, June 5, 1976, or that of W. Abraham and G. Barnikow, Tetrahedron 29, 691–7 (1973).

The disclosures of all references cited above are herein incorporated by reference.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged.

This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

In the following examples, all parts are by weight and temperatures in °C. unless otherwise indicated.

EXAMPLE 1

Methyl o-Isocyanatosulfonylbenzeneacetate

A mixture of 22.9 g methyl o-aminosulfonylbenzeneacetate, 13.5 g n-butyl isocyanate, 15.2 g potassium carbonate and 250 ml methyl ethyl ketone was stirred and refluxed for three hours. The reaction mixture was cooled, poured into 1250 g of ice-water, and acidified to pH 1.5 with concentrated HCl. The product was filtered, washed and dried. The crude product was recrystallized from 1-chlorobutane to yield 24.3 g of purified N-(n-butyl)sulfonylurea derivative of methyl o-isocyanatosulfonylbenzeneacetate, m.p. 164°–166° (dec.).

To 16.4 g of the above N-(n-butyl)sulfonylurea derivative was added 150 ml of xylene and 0.2 g DABCO. The mixture was stirred and heated until 30 ml of xylene had been distilled off. The distillation head was replaced with a dry-ice reflux condenser, and then phosgene was slowly passed into the reaction mixture, which was maintained at 130°–138°, over about one hour. When no more phosgene was taken up, the mixture was heated at 132°–133° under slow phosgene reflux for one hour longer. The reaction mixture was cooled to room temperature, filtered to remove some solids and concentrated in vacuo to yield 25.0 g of the desired sulfonyl isocyanate product as an oil.

EXAMPLE 2

Methyl 2-[[(4,6-dimethoxypyrimidin-2-yl)aminocarbonyl]aminosulfonyl]benzeneacetate The 25 g of methyl o-isocyanatosulfonylbenzeneacetate from Example 1 was dissolved in 150 ml dry acetonitrile, and 0.2 g DABCO was added. To the stirred solution at 27° was added all at once 7.6 g of 2-amino-4,6-dimethoxypyrimidine. The temperature rose rapidly to 42°. The reaction mixture was then stirred and heated at 48°–50° for two hours, and stirred at ambient temperature for a further sixteen hours. The product was recovered by filtration and dried; 16.3 g of the desired sulfonylurea was obtained, m.p. 193°–196° (dec.). The product absorbed in the IR at 1730, 1610 and 1570 cm$^{-1}$. It showed NMR absorption at δ3.8 (s, 3H), methyl ester: δ4.1 (s, 6H), pyrimidine methoxyl groups; δ4.3 (s, 2H), benzeneacetic group; δ6.2 (s, 1H), pyrimidine ring hydrogen; δ7.3–8.5 (m, 4H), aromatic hydrogens.

Anal. Calcd. for $C_{16}H_{18}N_4O_7S$: C, 46.82; H, 4.42; N, 13.66; S, 7.81. Found: C, 46.9, 47.0; H, 4.4, 4.4; N, 14.0, 14.0; S, 8.3, 8.0.

All data are consistent with the structure of the desired sulfonylurea.

EXAMPLE 3

2-[[(4,6-Dimethoxypyrimidin-2yl)aminocarbonyl-]aminosulfonyl]benzeneacetic acid 1.03 g of the product of Example 2 was added to a stirred solution of 0.5 g of commercial 50% aqueous sodium hydroxide mixed with 25 ml of water at ambient temperature. A clear solution was obtained after a few minutes. Stirring at ambient temperature was maintained for two hours. 2 N hydrochloric acid was added dropwise to pH 2, causing the desired product to precipitate out. The solid product was filtered, washed and dried; 0.95 g was obtained, m.p. 173°–175° (dec.). The product absorbed in the IR at 1730, 1690, 1610 and 1580 cm$^{-1}$. It showed NMR absorption at δ4.0 (s, 6H), pyrimidine methoxyl groups; δ4.1 (s, 2H), benzeneacetic group; δ5.9 (s, 1H), pyrimidine ring hydrogen; δ7.3–8.4 (m, 4H), aromatic hydrogens; δ10.5 (s, 1H), carboxylic acid. The spectral data are consistent with the structure of the desired sulfonylurea.

EXAMPLE 4

Methyl 2-[[(4-methoxy-6-methyl-1,3,5-triazin-2-yl)aminocarbonyl]aminosulfonyl]benzeneacetate 2.3 g Methyl o-isocyanatosulfonylbenzeneacetate prepared as described in Example 1, and 0.03 g DABCO were dissolved in 30 ml dry acetonitrile. 1.2 g of 2-Amino-4-methoxy-6-methyl-1,3,5-triazine was added all at once to the stirred solution, which was heated for two hours at 50°–55°, then for sixteen hours at ambient temperature. The reaction mixture was filtered and the solids obtained were washed and dried (1.0 g). The solids, which were a mixture of the desired product and unreacted 2-amino-4-methoxy-6-methyl-1,3,5-triazine, were dissolved in 100 ml methylene chloride and washed with 0.3 N hydrochloric acid, which removed unreacted aminotriazine. Evaporation of the methylene chloride yielded 0.7 g of the desired sulfonylurea; m.p. 162°–165° (dec.). The product showed NMR absorption at δ2.9 (s, 3H), triazine methyl; δ3.9 (s, 3H), methyl ester; δ4.35 (s, 2H), benzeneacetic group; δ4.4 (s, 3H), triazine methoxyl; δ7.4–8.6 (m, 4H) aromatic hydrogens; consistent with the structure of the desired sulfonylurea.

EXAMPLE 5

Ethyl 2-[[(4,6-dimethoxypyrimidin-2-yl)aminocarbonyl]aminosulfonyl]benzeneacetate Following the procedure of Example 1, ethyl o-aminosulfonylbenzeneacetate was reacted with n-butyl isocyanate to form the N-(n-butyl)sulfonylurea derivative; m.p. 140°–142°.

Following the procedure of Example 1, the N-(n-butyl)sulfonylurea derivative was reacted with phosgene to form ethyl o-isocyanotosulfonylbenzeneacetate, an oil. 1.35 g of Ethyl o-isocyanatosulfonylbenzeneacetate and 0.015 g of DABCO were dissolved in 15 ml acetonitrile. 0.8 g of 2-Amino-4,6-dimethoxypyrimidine was added all at once, and the reaction mixture was stirred for sixteen hours at ambient temperature. The product was recovered by filtration; 1.2 g of the desired sulfonylurea was obtained, m.p. 168°–172° (dec.). The product showed NMR absorption at δ1.1–1.4 (t, 3H), methyl group of ethyl ester; δ4.2 (s, 6H), methoxyl groups of pyrimidine; δ4.1–4.4 (q, 2H), methylene of ethyl ester; δ4.3 (s, 2H), methylene of benzene acetic group; δ6.3 (s, 1H), pyrimidine hydrogen; δ7.4–8.4 (m, 4H), aromatic hydrogens; consistent with the structure of the desired sulfonylurea.

EXAMPLE 6

Methyl 2-[[(4,6-dichloropyrimidin-2yl)aminocarbonyl]aminosulfonyl]benzeneacetate To 2.3 g of 2-(aminosulfonyl)benzeneacetic acid methyl ester in 30 ml of acetonitrile was added 1.5 g of anhydrous potassium carbonate and 1.6 g of 4,6-dichloropyrimidin-2-yl isocyanate. The mixture was stirred at room temperature for 6 hours, diluted with 250 g of water and acidified to a pH of about 4. The resulting solid was filtered and dried to yield 1.6 g of methyl 2-[[(4,6-dichloropyrimidin-2-yl)aminocarbonyl]aminosulfonyl]benzeneacetate, a pale yellow solid, m.p. 115°–118° C. It showed infrared absorption peaks at 1730, 1600 and 1560 cm$^{-1}$ and nuclear magnetic resonance peaks at 3.7 ppm, methyl ester group; 4.2 ppm, benzeneacetic group; 6.9 ppm, pyrimidin H; 7.4–7.6 ppm, aromatic hydrogens; consistent for the product.

EXAMPLE 7

Methyl 2-[[(4,6-dimethoxy-1,3,5-triazin-2yl)aminothioxomethyl]aminosulfonyl]benzeneacetate To 1.1 g of 2-(aminosulfonyl)benzeneacetic acid methyl ester in 25 ml of ethyl methyl ketone was added 1.9 g of anhydrous potassium carbonate and 1.0 g of 2,4-dimethoxy-1,3,5-triazinyl-6-isothiocyanate. The mixture was stirred at room temperature for 24 hours and then diluted with 200 g of ice-water. The solution was acidified with dilute HCl to a pH of about 4. The resulting product was filtered and dried to give 1.2 g of white solid, m.p. 164°–168° C. It showed infrared absorption peaks at 1750, 1630 and 1570 cm$^{-1}$ and nuclear magnetic resonance peaks at 3.9, 4.4, 4.5 and 7.6 ppm, consistent for the product.

EXAMPLE 8

2-[[(4,6-Dimethoxypyrimidin-2-yl)aminocarbonyl]aminosulfonyl]-N,N-tetramethylenebenzeneacetamide To 1.42 g of pyrrolidine in 100 ml of dry methylene chloride at room temperature was added 10 ml of commercial two molar trimethylaluminum in toluene. The temperature rose by 5°. After the resulting solution had been stirred for ten minutes, 4.1 g of the product of Example 2 was added portionwise over five minutes. The reaction mixture was stirred and refluxed for sixteen hours. 200 ml of water and 10 ml of concentrated hydrochloric acid was then added to the reaction mixture, the methylene chloride layer was separated, dried by addition of magnesium sulfate, and the solvent removed by distillation at reduced pressure. The residue was a gum. Trituration of the gum with 1-chlorobutane resulted in the formation of crystals. The product was filtered, washed and dried, 3.8 g was obtained; m.p. 133°–135° (dec.). The product absorbed in the IR at 1720, 1650, 1600 and 1550 cm$^{-1}$. It showed NMR absorption at δ2.1–2.5 (m, 4H), pyrrolidine hydrogens at positions 3 and 4; δ3.7–4.1 (m, 4H), pyrrolidine hydrogens at positions 2 and 5; δ4.1 (s, 6H), pyrimidine methoxyl groups, δ4.6 (s, 2H), benzeneacetic group; δ6.2 (s, 1H), pyrimidine ring hydrogen; δ7.4–8.4 (m, 4H) aromatic hydrogens. The spectral data are consistent with the structure of the desired sulfonylurea.

Using the general procedures described above, and those of Examples 1 to 8, the following compounds can be made by one skilled in the art.

TABLE I

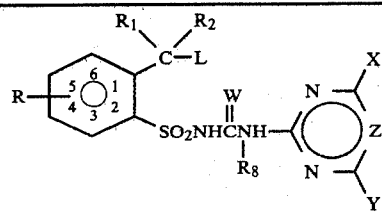

| L | R | $R_1$ | $R_2$ | X | Y | Z | $R_8$ | W | Phys. Prop. (m.p.) |
|---|---|---|---|---|---|---|---|---|---|
| $CO_2CH_3$ | H | H | H | $CH_3$ | $CH_3$ | N | H | O | |
| $CO_2CH_3$ | H | H | H | $CH_3$ | $CH_3O$ | CH | H | O | 194–196° (dec) |
| $CO_2CH_3$ | H | H | H | $CH_3$ | $CH_3$ | CH | H | O | 195–198° (dec) |
| $CO_2CH_3$ | H | H | H | $CH_3O$ | $CH_3O$ | N | H | O | 182–184° (dec) |
| $CO_2C_2H_5$ | H | H | H | $CH_3$ | $CH_3$ | CH | H | O | |
| $CO_2C_2H_5$ | H | H | H | $CH_3$ | $CH_3O$ | CH | H | O | 168–170° (dec) |
| $CO_2C_2H_5$ | H | H | H | $CH_3O$ | $CH_3O$ | N | H | O | |
| $CO_2C_2H_5$ | H | H | H | $CH_3$ | $CH_3$ | N | H | O | |
| $CO_2CH(CH_3)_2$ | H | H | H | $CH_2CH_3$ | $OCH_3$ | N | H | O | |
| $CO_2$—n-$C_4H_9$ | H | H | H | $CH_2OCH_3$ | $OCH_3$ | N | H | O | |
| $CO_2C_2H_5$ | H | H | H | $CH_3$ | $CH_3O$ | N | H | O | |
| $CO_2$—$CH_2$—CH=$CH_2$ | H | H | H | $CH_3O$ | $CH_3O$ | CH | H | O | 174–177° (dec) |
| $CO_2$—$CH_2$—CH=$CH_2$ | H | H | H | $CH_3$ | $CH_3O$ | N | H | O | |
| $CO_2CH(CH_3)_2$ | H | H | H | $CH_3$ | $CH_3O$ | CH | H | O | 135–150° |
| $CO_2CH(CH_3)_2$ | H | H | H | $CH_3O$ | $CH_3O$ | CH | H | O | 165–168° (dec) |
| $CO_2H$ | H | H | H | $CH_3$ | $CH_3$ | CH | H | O | 162–164° (dec) |
| $CO_2H$ | H | H | H | $CH_3O$ | $CH_3$ | CH | H | O | 207–209° (dec) |
| $CO_2H$ | H | H | H | $CH_3O$ | $CH_3O$ | CH | H | O | 173–175° (dec) |
| $CO_2H$ | H | H | H | $CH_3$ | $CH_3$ | N | H | O | |
| $CO_2H$ | H | H | H | $CH_3O$ | $CH_3$ | N | H | O | 142–144° (dec) |
| $CO_2H$ | H | H | H | $CH_3O$ | $CH_3O$ | N | H | O | 155–157° (dec) |
| $CO_2CH_3$ | H | $CH_3$ | H | $CH_3$ | $CH_3$ | CH | H | O | |
| $CO_2CH_3$ | H | $CH_3$ | H | $CH_3$ | $CH_3O$ | CH | H | O | |
| $CO_2CH_3$ | H | $CH_3$ | H | $CH_3O$ | $CH_3O$ | CH | H | O | |
| $CO_2CH_3$ | H | $CH_3$ | H | $CH_3$ | $CH_3$ | N | H | O | |
| $CO_2CH_3$ | H | $CH_3$ | H | $CH_3$ | $CH_3O$ | N | H | O | |
| $CO_2CH_3$ | H | $CH_3$ | H | $CH_3O$ | $CH_3O$ | N | H | O | |
| $CO_2CH_3$ | H | $CH_3CH_2$ | H | $CH_3O$ | $CH_3O$ | CH | H | O | |
| $CO_2CH_3$ | H | n-$C_4H_9$ | H | $CH_3O$ | $CH_3O$ | CH | H | O | |
| $CO_2CH_3$ | H | $CH_3$ | $CH_3$ | $CH_3O$ | $CH_3O$ | CH | H | O | |
| $CO_2CH_3$ | 4-F | H | H | $CH_3O$ | $CH_3O$ | CH | H | O | |
| $CO_2CH_3$ | 4-Cl | H | H | $CH_3O$ | $CH_3$ | N | H | O | |
| $CO_2CH_3$ | 5-Br | H | H | $CH_3O$ | $CH_3O$ | CH | H | O | |
| $CO_2CH_3$ | 4-$CF_3$ | H | H | $CH_3O$ | $CH_3$ | N | H | O | |
| $CO_2CH_3$ | 4-$CH_3$ | H | H | $CH_3O$ | $CH_3$ | N | H | O | |
| $CO_2CH_3$ | 5-$OCH_3$ | H | H | $CH_3O$ | $CH_3O$ | CH | H | O | |
| $CO_2CH_3$ | 4-n-$C_3H_7$ | H | H | $CH_3O$ | $CH_3$ | N | H | O | |
| $CO_2CH_3$ | 5-$CH_3CH_2CH_2O$ | H | H | $CH_3O$ | $CH_3O$ | CH | H | O | |
| $CO_2CH_3$ | 3-Cl | H | H | $CH_3O$ | $CH_3$ | N | H | O | |
| $CO_2CH_3$ | 5-Cl | H | H | $CH_3O$ | $CH_3O$ | CH | H | O | |
| $CO_2CH_3$ | 6-Cl | H | H | $CH_3O$ | $CH_3$ | N | H | O | |
| $CO_2CH_3$ | H | H | H | $CH_3O$ | $CH_3$ | N | $CH_3$ | O | |
| $CO_2CH_3$ | H | H | H | $CH_3O$ | $CH_3O$ | CH | $CH_3$ | O | |
| $CO_2CH_3$ | H | H | H | $CH_3$ | $CH_3$ | CH | $CH_3$ | O | |
| $CO_2CH_3$ | H | H | H | $CH_3$ | $CH_3$ | N | $CH_3$ | O | |
| $CO_2CH_3$ | H | H | H | $CH_3O$ | $CH_3O$ | N | $CH_3$ | O | |
| $CO_2CH_3$ | H | H | H | $CH_3O$ | $CH_3$ | CH | $CH_3$ | O | |
| $CO_2CH_3$ | H | H | H | $CH_3O$ | $CH_3$ | N | $CH_3O$ | O | |
| $CO_2CH_3$ | H | H | H | $CH_3O$ | $CH_3O$ | CH | $CH_3O$ | O | |
| $CO_2$—$CH_2$—$CH_2$—CH=$CH_2$ | H | H | H | $CH_3O$ | $CH_3O$ | CH | H | O | |

TABLE I-continued

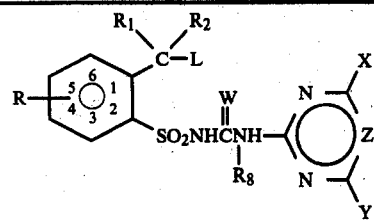

| L | R | R₁ | R₂ | X | Y | Z | R₈ | W | Phys. Prop. (m.p.) |
|---|---|---|---|---|---|---|---|---|---|
| CO₂—CH₂—C(CH₃)=CH₂ | H | H | H | CH₃O | CH₃ | N | H | O | |
| CO₂—CH₂CH₂Cl | H | H | H | CH₃O | CH₃O | CH | H | O | |
| CO₂—CH₂—CH₂OCH₃ | H | H | H | CH₃O | CH₃ | N | H | O | |
| CO₂CH₃ | H | H | H | CH₃ | CH₃ | CH | H | S | |
| CO₂CH₃ | H | H | H | CH₃ | CH₃O | CH | H | S | |
| CO₂CH₃ | H | H | H | CH₃O | CH₃O | CH | H | S | |
| CO₂CH₃ | H | H | H | CH₃ | CH₃ | N | H | S | |
| CO₂CH₃ | H | H | H | CH₃ | CH₃O | N | H | S | |
| CO₂CH₃ | H | CH₃ | H | CH₃ | CH₃ | CH | H | S | |
| CO₂CH₃ | H | CH₃ | H | CH₃O | CH₃O | N | H | S | |
| CO₂CH₃ | 4-Cl | H | H | CH₃ | CH₃ | CH | H | S | |
| CO₂CH₃ | 5-Cl | H | H | CH₃O | CH₃O | N | H | S | |
| CO₂CH₂CH₃ | H | H | H | CH₃ | CH₃ | CH | H | S | |
| CO₂CH₂CH₃ | H | H | H | CH₃O | CH₃O | N | H | S | |
| CO₂—CH₂—CH=CH₂ | H | H | H | CH₃ | CH₃ | CH | H | S | |
| CO₂—CH₂—CH=CH₂ | H | H | H | CH₃O | CH₃O | N | H | S | |
| C(O)—N(CH₃)₂ | H | H | H | OCH₃ | CH₃ | N | H | O | |
| C(O)N(C₂H₅)₂ | H | H | H | OC₂H₅ | CH₃ | N | H | O | |
| C(O)—N(CH₃)(C₂H₅) | H | H | H | O—n-C₃H₇ | CH₃ | N | H | O | |
| C(O)—N(H)(CH₃) | H | H | H | O—i-C₃H₇ | CH₃ | N | H | O | |
| C(O)—N(H)(C₂H₅) | H | H | H | OCH₃ | CH₃ | N | H | O | |
| C(O)—N(H)(CH₂CH₂CH₃) | H | H | H | H | CH₃ | N | H | O | |
| C(O)—NH₂ | H | H | H | OCH₃ | OCH₃ | CH | H | O | |
| C(O)—N(CH₂CH₂CH₂CH₃)₂ | H | H | H | OCH₃ | OCH₃ | CH | H | O | |
| C(O)—N(CH₃)—OCH₃ | H | H | H | OCH₃ | OCH₃ | CH | H | O | |
| C(O)—N(CH₃)—OCH₃ | H | H | H | OCH₃ | CH₃ | N | H | O | |

TABLE I-continued

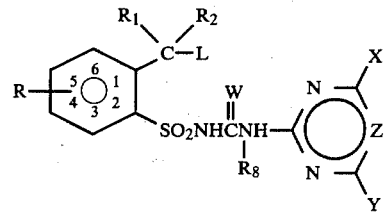

| L | R | R$_1$ | R$_2$ | X | Y | Z | R$_8$ | W | Phys. Prop. (m.p.) |
|---|---|---|---|---|---|---|---|---|---|
| O=C-N(CH$_2$CH$_2$)$_2$ (pyrrolidine) | H | H | H | OCH$_3$ | OCH$_3$ | CH | H | O | 133–135° (dec) |
| O=C-N(CH$_2$CH$_2$)$_2$CH$_2$ (piperidine) | H | H | H | OCH$_3$ | OCH$_3$ | CH | H | O | |
| O=C-N(CH$_2$CH$_2$)$_2$O (morpholine) | H | H | H | CH$_3$ | OCH$_3$ | CH | H | O | |
| O=C-N(H)-CH(CH$_3$)CH$_2$-CH$_3$ | H | H | H | H | CH$_3$ | CH | H | O | |
| O=C-NHCH$_2$CH(CH$_3$)$_2$ | H | H | H | CH$_3$ | CH$_3$ | CH | H | O | |
| O=CN(CH$_3$)$_2$ | H | H | H | H | CH$_3$ | CH | H | O | |
| O=CN(C$_2$H$_5$)$_2$ | H | H | H | H | CH$_3$ | CH | H | O | |
| O=C-N(CH$_3$)(n-C$_3$H$_7$) | H | H | H | H | CH$_3$ | CH | H | O | |
| O=C-N(C$_2$H$_5$)(n-C$_4$H$_9$) | H | H | H | H | CH$_3$ | CH | H | O | |
| O=CN(CH$_3$)$_2$ | H | H | H | CH$_3$ | OCH$_3$ | N | H | O | |
| O=CNHCH$_3$ | H | H | H | CH$_3$ | OCH$_3$ | N | H | O | |
| O=CN(C$_2$H$_5$)$_2$ | H | H | H | CH$_3$ | OCH$_3$ | N | H | O | |
| O=C-N(CH$_3$)(C$_2$H$_5$) | H | H | H | CH$_3$ | OCH$_3$ | CH | H | O | |
| O=C-N(CH$_3$)(n-C$_3$H$_7$) | H | H | H | CH$_3$ | OCH$_3$ | CH | H | O | |
| O=C-N(CH$_3$)(n-C$_4$H$_9$) | H | H | H | CH$_3$ | OCH$_3$ | CH | H | O | |

TABLE I-continued

| L | R | R$_1$ | R$_2$ | X | Y | Z | R$_8$ | W | Phys. Prop. (m.p.) |
|---|---|---|---|---|---|---|---|---|---|
| $\overset{O}{\underset{\|}{C}}OCH_3$ | H | H | H | Cl | OCH$_3$ | N | H | O | |
| $\overset{O}{\underset{\|}{C}}OCH_3$ | H | H | H | Br | OCH$_3$ | CCl | H | O | |
| $\overset{O}{\underset{\|}{C}}OCH_3$ | H | H | H | Cl | CH$_3$ | CBr | H | O | |
| $\overset{O}{\underset{\|}{C}}OCH_3$ | H | H | H | Br | CH$_3$ | CH | H | O | |
| $\overset{O}{\underset{\|}{C}}-OCH_3$ | H | H | H | H | CH$_3$ | CCN | H | O | |
| $\overset{O}{\underset{\|}{C}}-OCH_3$ | H | H | H | H | CH$_3$ | CCH$_3$ | H | O | |
| $\overset{O}{\underset{\|}{C}}-OCH_3$ | H | H | H | H | CH$_3$ | CCH$_2$CH$_2$Cl | H | O | |
| $\overset{O}{\underset{\|}{C}}-OCH_3$ | H | H | H | H | CH$_3$ | CCH$_2$CH=CH$_2$ | H | O | |
| $\overset{O}{\underset{\|}{C}}N(CH_3)_2$ | 4-F | H | H | CH$_3$ | OCH$_3$ | CH | H | O | |
| $\overset{O}{\underset{\|}{C}}N(CH_3)_2$ | 5-Cl | H | H | CH$_3$ | OCH$_3$ | CH | H | O | |
| $\overset{O}{\underset{\|}{C}}N(CH_3)_2$ | 4-Br | H | H | CH$_3$ | OCH$_3$ | CH | H | O | |
| $\overset{O}{\underset{\|}{C}}N(CH_3)_2$ | 4-NO$_2$ | H | H | CH$_3$ | OCH$_3$ | CH | H | O | |
| $\overset{O}{\underset{\|}{C}}N(CH_3)_2$ | 5-CF$_3$ | H | H | CH$_3$ | OCH$_3$ | N | H | O | |
| $\overset{O}{\underset{\|}{C}}N(CH_3)_2$ | 5-OCH$_3$ | H | H | CH$_3$ | OCH$_3$ | N | H | O | |
| $\overset{O}{\underset{\|}{C}}N(CH_3)_2$ | 5-OCH$_2$CH$_2$CH$_3$ | H | H | CH$_3$ | OCH$_3$ | N | H | O | |
| CN | H | H | H | H$_3$ | OCH$_3$ | N | H | O | |
| CN | H | H | H | CH$_3$ | OCH$_3$ | CH | H | O | |
| CN | 4-Cl | H | H | CH$_3$ | OCH$_3$ | CH | H | O | |
| CN | 4-F | H | H | CH$_3$ | OCH$_3$ | CH | H | O | |
| CN | 4-Br | H | H | CH$_3$ | OCH$_3$ | CH | H | O | |
| CN | 4-OC$_2$H$_5$ | H | H | C$_2$H$_5$ | OCH$_3$ | CH | H | O | |
| CN | 3-Cl | H | H | OC$_2$H$_5$ | CH$_3$ | CH | H | O | |
| CN | 5-Cl | H | H | O—n-C$_3$H$_7$ | CH$_3$ | CH | H | O | |
| CN | 6-Cl | H | H | CF$_3$ | CH$_3$ | CH | H | O | |
| CN | 4-NO$_2$ | H | H | CH$_3$S | CH$_3$ | CH | H | O | |

TABLE I-continued

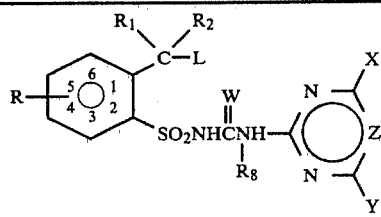

| L | R | R₁ | R₂ | X | Y | Z | R₈ | W | Phys. Prop. (m.p.) |
|---|---|---|---|---|---|---|---|---|---|
| CN | 4-CF₃ | H | H | CH₃OCH₂ | CH₃ | CH | H | O | |
| CN | H | CH₃ | CH₃ | CH₃O | CH₃ | N | H | O | |
| CN | H | n-C₄H₉ | H | CH₃O | CH₃O | N | H | O | |
| CN | H | n-C₃H₇ | H | CH₃O | CH₃O | N | H | O | |
| CN | H | C₂H₅ | H | CH₃O | CH₃O | N | H | O | |
| CN | H | H | H | H | CH₃ | CCl | H | O | |
| CN | H | H | H | H | CH₃ | CBr | H | O | |
| CN | H | H | H | CH₃ | CH₃ | CCN | H | O | |
| CN | H | H | H | CH₃ | CH₃ | CCH₃ | H | O | |
| CN | H | H | H | CH₃ | CH₃ | CCH₂CH₃ | H | O | |
| CN | H | H | H | CH₃ | CH₃ | CCH₂CH₂Cl | H | O | |
| CN | H | H | H | H | CH₃ | CCH₂CH=CH₂ | H | O | |
| CN | H | H | H | H | CH₃ | CCH₃ | H | O | |
| CN | H | H | H | CH₃ | CH₃ | CH | H | S | |
| CN | H | H | H | CH₃O | CH₃O | N | H | S | |
| CN | H | H | H | CH₃ | CH₃ | N | H | O | |
| CN | H | H | H | CH₃ | CH₃ | CH | H | O | |
| CN | H | H | H | CH₃O | CH₃O | N | H | O | |
| CN | H | H | H | CH₃O | CH₃O | CH | H | O | |
| CN | H | H | H | CH₃ | CH₃ | CH | CH₃ | O | |
| CN | H | H | H | CH₃ | CH₃ | N | CH₃ | O | |
| CN | H | H | H | CH₃O | CH₃O | CH | CH₃ | O | |
| CN | H | H | H | CH₃O | CH₃O | N | CH₃ | O | |
| CN | H | H | H | CH₃O | CH₃ | CH | CH₃ | O | |
| CN | H | H | H | CH₃O | CH₃ | N | CH₃ | O | |
| CN | H | H | H | CH₃O | CH₃O | CH | CH₃O | O | |
| CN | H | H | H | CH₃O | CH₃ | N | CH₃O | O | |
| O∥C—N(CH₃)₂ | H | H | H | CH₃O | CH₃ | CH | H | O | |
| O∥C—N(CH₃)₂ | H | H | H | CH₃ | CH₃ | CH | H | O | |
| O∥C—N(CH₃)₂ | H | H | H | CH₃ | CH₃ | N | H | O | |
| O∥C—N(CH₃)₂ | H | H | H | CH₃O | CH₃O | CH | H | O | |
| O∥C—N(CH₃)₂ | H | H | H | CH₃O | CH₃O | N | H | O | |
| O∥C—N(CH₃)₂ | H | H | H | CH₃ | CH₃ | CH | CH₃ | O | |
| O∥C—N(CH₃)₂ | H | H | H | CH₃ | CH₃ | N | CH₃ | O | |
| O∥C—N(CH₃)₂ | H | H | H | CH₃O | CH₃ | CH | CH₃ | O | |
| O∥C—N(CH₃)₂ | H | H | H | CH₃0 | CH₃ | N | CH₃ | 0 | |
| O∥C—N(CH₃)₂ | H | H | H | CH₃O | CH₃O | CH | CH₃ | O | |

TABLE I-continued

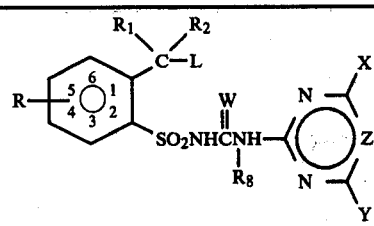

| L | R | R₁ | R₂ | X | Y | Z | R₈ | W | Phys. Prop. (m.p.) |
|---|---|---|---|---|---|---|---|---|---|
| $\underset{C-N(CH_3)_2}{\overset{O}{\parallel}}$ | H | H | H | CH₃O | CH₃O | N | CH₃ | O | |
| $\underset{C-N(CH_3)_2}{\overset{O}{\parallel}}$ | H | H | H | CH₃O | CH₃O | CH | CH₃O | O | |
| $\underset{C-N(CH_3)_2}{\overset{O}{\parallel}}$ | H | H | H | CH₃O | CH₃ | N | CH₃O | O | |
| $\underset{C-N(CH_3)_2}{\overset{O}{\parallel}}$ | H | H | H | CH₃ | CH₃ | CH | H | S | |
| $\underset{C-N(CH_3)_2}{\overset{O}{\parallel}}$ | H | H | H | CH₃O | CH₃O | N | H | S | |

TABLE II

| L | R | R₁ | R₂ | Y' | Q | R₈ | W |
|---|---|----|----|----|---|----|---|
| CO₂CH₃ | H | H | H | CH₃ | O | H | O |
| CO₂C₂H₅ | H | CH₃ | CH₃ | CH₃O | O | H | O |
| CN | H | H | CH₃ | CH₃CH₂O | O | H | O |
| $\underset{CN(CH_3)_2}{\overset{O}{\parallel}}$ | H | H | H | H | O | H | O |
| CO₂—i-C₃H₇ | H | H | H | CH₃ | CH₂ | H | O |
| CO₂—n-C₄H₉ | H | H | H | CH₃O | CH₂ | H | O |
| CO₂CH₃ | H | H | H | CH₃ | O | CH₃ | O |
| CO₂CH₃ | H | H | H | CH₃O | CH₂ | CH₃O | O |
| CO₂CH₃ | H | H | H | CH₃ | CH₂ | CH₃ | O |
| CO₂CH₃ | H | H | H | CH₃O | O | CH₃O | O |
| CO₂CH₃ | H | H | H | CH₃ | CH₂ | H | S |
| CO₂CH₃ | H | H | H | CH₃O | O | H | S |

TABLE III

| L | R | R₁ | R₂ | R₈ | Y' | W |
|---|---|----|----|----|----|---|
| CO₂CH₃ | H | H | H | H | H | O |
| CO₂CH₃ | H | H | H | H | CH₃ | O |
| CO₂CH₃ | H | H | H | H | CH₃O | O |
| CO₂CH₃ | H | CH₃ | H | H | CH₃CH₂O | O |
| CO₂CH₃ | H | H | H | H | CH₃ | S |
| CO₂CH₃ | H | H | H | H | CH₃O | S |
| CO₂CH₂CH₃ | H | CH₃ | H | CH₃ | CH₃ | O |
| CN | H | H | H | H | CH₃O | O |
| CON(CH₃)₂ | H | H | H | H | CH₃ | O |

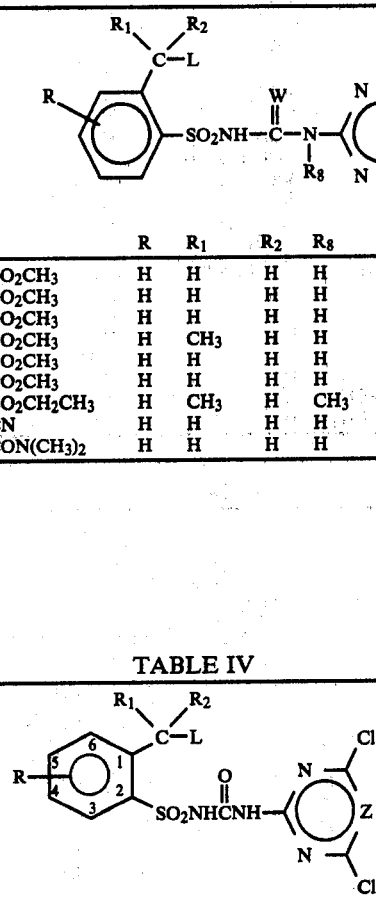

TABLE IV

| L | R | R₁ | R₂ | Z |
|---|---|----|----|----|
| CO₂CH₃ | H | H | H | N |
| CO₂CH₃ | H | H | H | CH |
| CO₂C₂H₅ | H | CH₃ | H | N |

TABLE IV-continued

[Structure: phenyl ring with R at position 4-5, C(R1)(R2)-L at position 1, SO2NHC(O)NH-pyrimidine/triazine (with Cl at both positions and Z in between) at position 2]

| L | R | $R_1$ | $R_2$ | Z |
|---|---|---|---|---|
| $\overset{O}{\underset{}{C}}-N(CH_3)_2$ | H | H | H | CH |
| $\overset{O}{\underset{}{C}}-N\overset{CH_3}{\underset{C_2H_5}{}}$ | H | $CH_3CH_2CH_2$ | H | N |
| $\overset{O}{\underset{}{C}}-N\overset{CH_3}{\underset{i\text{-}C_3H_7}{}}$ | H | $(CH_3)_2CH$ | H | CH |
| CN | H | H | H | N |
| $CO_2$—n-$C_3H_7$ | H | $CH_3$—CH—$CH_2$ <br>           $CH_3$ | H | CH |
| $CO_2$—n-$C_4H_9$ | H | $C(CH_3)_3$ | H | N |
| $CO_2CH_3$ | H | $HC(CH_3)CH_2CH_3$ | H | CH |
| $CO_2CH_3$ | 4-F | H | H | N |
| $CO_2CH_3$ | 4-Cl | H | H | CH |
| $CO_2CH_3$ | 4-Br | H | H | N |
| $CO_2CH_3$ | 4-$NO_2$ | H | H | CH |
| $CO_2CH_3$ | 4-$CF_3$ | H | H | N |
| $CO_2CH_3$ | 5-$CH_3$ | H | H | CH |
| $CO_2CH_3$ | 6-$CH_3CH_2$ | H | H | N |
| $CO_2CH_3$ | 5-$CH_3CH_2CH_2$ | H | H | CH |
| $CO_2CH_3$ | 5-$(CH_3)_2CH$ | H | H | N |
| $CO_2CH_3$ | 3-$CH_3O$ | H | H | CH |
| $CO_2CH_3$ | 4-$CH_3CH_2O$ | H | H | N |
| $CO_2CH_3$ | 4-$CH_3CH_2CH_2O$ | H | H | CH |
| $CO_2CH_2CH(CH_3)_2$ | 4-$(CH_3)_2CHO$ | H | H | N |
| $CO_2$—i-$C_3H_7$ | H | H | H | CH |
| $CO_2$—i-$C_3H_7$ | H | H | H | N |
| $CO_2$—sec-$C_4H_9$ | H | H | H | CH |
| $CO_2CH_2CH_3$ | H | $CH_3$ | $CH_3$ | N |
| $CO_2CH_2CH_3$ | H | H | H | CH |
| $CO_2$—$CH_2$-CH=$CH_2$ | H | H | H | N |
| $CO_2$—$CH_2$-CH=$CH_2$ | H | H | H | CH |

TABLE V

[Structure: phenyl ring with R at position 4-5, C(R1)(R2)-CO2R10 at position 1, CO2NCO at position 2]

| R | $R_1$ | $R_2$ | $R_{10}$ |
|---|---|---|---|
| H | H | H | $CH_3$ |
| H | H | H | $CH_3CH_2$ |
| H | H | H | $(CH_3)_2CH$ |
| H | H | H | $CH_3CH_2CH_2CH_2$ |
| H | H | H | $CH_2$=CH—$CH_2$ |
| H | $CH_3$ | H | $CH_3$ |
| 4-Cl | H | H | $CH_3$ |
| 4-$NO_2$ | H | H | $CH_3$ |
| 4-$CF_3$ | H | H | $CH_3$ |
| 4-$CH_3$ | H | H | $CH_3$ |
| 4-$CH_3O$ | H | H | $CH_3$ |
| 5-F | H | H | $CH_3CH_2$ |
| 5-Br | H | H | $CH_3CH_2$ |
| H | $CH_3CH_2$ | $CH_3$ | $CH_3$ |
| H | $CH_3CH_2CH_2CH_2$ | H | $CH_3$ |

TABLE V-continued

[Structure: benzene ring numbered 1-6 with R at position 4/5, and at position 1 substituents: $R_1$, $R_2$, $C-CO_2R_{10}$, and $CO_2NCO$ at position 2]

| R | $R_1$ | $R_2$ | $R_{10}$ |
|---|---|---|---|
| 4-$CH_3CH_2CH_2$ | H | H | $CH_3$ |
| 4-$CH_3CH_2CH_2O$ | H | H | $CH_3$ |
| H | H | H | $CH_3-CH=CH-CH_2$ |
| H | H | H | $ClCH_2CH_2$ |
| H | H | H | $CH_3OCH_2CH_2$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further information. The formulations, broadly, contain about 0.1% to 99% by weight of active ingredients(s) and at least one of (a) about 0.1% to 20% surfactant(s) and (b) about 1% to 99.9% solid or liquid diluent(s). More specifically, they will contain these ingredients in the following approximate proportions:

TABLE VI

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 9

| Wettable Powder | |
|---|---|
| 2-[[(4,6-dimethoxypyrimidin-2-yl)aminocarbonyl]aminosulfonyl]benzeneacetic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 10

| Wettable Powder | |
|---|---|
| 2-[[(4,6-dimethylpyrimidin-2-yl)aminocarbonyl]aminosulfonyl]benzeneacetic acid, methyl ester | 50% |
| sodium alkylnaphthalenesulfonate | 2% |

| Wettable Powder | |
|---|---|
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

| Granule | |
|---|---|
| Wettable Powder of Example 10 | 5% |
| attapulgite granules (U.S.S. 20-40 mesh; 0.84-0.42 mm) | 95% |

A slurry of wettable powder containing ≈25% solids is sprayed on the surface of attapulgite granules in a double-cone blender. The granules are dried and packaged.

EXAMPLE 12

| Extruded Pellet | |
|---|---|
| 2-[[(4-methoxy-6-methylpyrimidin-2-yl)aminocarbonyl]-aminosulfonyl]benzeneacetic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

| Oil Suspension | |
|---|---|
| 2-[[(4,6-dimethoxy-1,3,5-triazin-2-yl)aminocarbonyl]-aminosulfonyl]benzeneacetic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

| Wettable Powder | |
|---|---|
| 2-[[(4-methoxy-6-methyl-1,3,5-triazin-2-yl)aminocarbonyl]aminosulfonyl] benzeneacetic acid, methyl ester | 20% |
| sodium alkylnaphthalenesulfonate | 4% |
| sodium ligninsulfonate | 4% |
| low viscosity methyl cellulose | 3% |

| Wettable Powder | |
|---|---|
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 15

| Low Strength Granule | |
|---|---|
| 2-[[(4,6-dimethoxypyrimidin-2-yl)aminocarbonyl]amino-sulfonyl]benzeneacetic acid, ethyl ester | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

| Aqueous Suspension | |
|---|---|
| 2-[[(4-methoxy-6-methylpyrimidin-2-yl)aminocarbonyl]-aminosulfonyl]benzeneacetic acid, ethyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

| Solution | |
|---|---|
| 2-[[(4,6-dimethoxypyrimidin-2-yl)aminocarbonyl]amino-sulfonyl]benzeneacetic acid, methyl ester, sodium salt | 5% |
| water | 95% |

The salt is added directly to the water with stirring to produce the solution, which may then be packaged for use.

EXAMPLE 18

| Low Strength Granule | |
|---|---|
| 2-[[(4,6-dimethylpyrimidin-2-yl)aminocarbonyl]amino-sulfonyl]benzeneacetic acid, methyl ester | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 19

| Granule | |
|---|---|
| 2-[[(4-methoxy-6-methylpyrimidin-2-yl)aminocarbonyl]-aminosulfonyl]benzeneacetic acid, methyl ester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 20

| High Strength Concentrate | |
|---|---|
| 2-[[(4,6-dimethoxy-1,3,5-triazin-2-yl)aminocarbonyl]-aminosulfonyl]benzeneacetic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 21

| Wettable Powder | |
|---|---|
| 2-[[(4-methoxy-6-methyl-1,3,5-triazin-2-yl)aminocarbonyl]aminosulfonyl]benzeneacetic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 22

| Wettable Powder | |
|---|---|
| 2-[[(4,6-dimethoxypyrimidin-2-yl)aminocarbonyl]aminosulfonyl]benzeneacetic acid, ethyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 23

| Oil Suspension | |
|---|---|
| 2-[[(4-methoxy-6-methylpyrimidin-2-yl)aminocarbonyl]-aminosulfonyl]benzeneacetic acid, ethyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are active herbicides. They have utility for pre- and/or post-emergence weed control in areas where control of broadleaf weeds and certain grass, or other weeds is desired, such as around fuel storage tanks, ammunition depots, industrial storage areas, oil-well sites, drive-in theaters, around billboards, highway and railroad structures. By properly selecting rate and time of application, compounds of this invention may be used to modify plant growth beneficially, and also to selectively control weeds in crops such as wheat and rice.

The precise amount of the compounds of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.02 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with the ureas: such as 3-(3,4-dichlorophenyl)-1,1-dimethylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamid); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl-diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)-one (m etribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl (methoxymethyl- )acetanilide (alachlor); and 1,1-dimethyl-3-(α,α,α-trifluoro-m-tolyl)-urea (fluometuron).

The activity of these compounds was discovered in greenhouse tests. The tests are described and data resulting from them are shown below.

Test A

Seeds of crabgrass (Digitaria spp.), barnyardgrass (*Echinochloa crusgalli*), wild oats (*Avena fatua*), cassia (*Cassia tora*), morningglory (Ipomoea sp.), cocklebur (Xanthium spp.), sorghum, corn, soybean, rice, wheat and nutsedge tubers (*Cyperus rotundus*) were planted in a growth medium and treated pre-emergence with the chemicals dissolved in a non-phytotoxic solvent. At the same time, cotton having five leaves (including cotyledonary ones), bush beans with the second trifoliate leaf expanding, crabgrass and barnyardgrass with two leaves, wild oats with one leaf, cassia with three leaves (including cotyledonary ones), morningglory and cocklebur with four leaves (including the cotyledonary ones), sorghum and corn with three leaves, soybean with two cotyledonary leaves, rice with two leaves, wheat with two leaves, and nutsedge with three to five leaves were sprayed. Treated plants and controls were maintained in a greenhouse for sixteen days, then all species were compared to controls and visually rated for response to treatment.

The ratings, shown in Table A, are based on a numerical scale extending from 0=no injury, to 10=complete kill. The accompanying descriptive symbols have the following meanings:
C=chlorosis/necrosis;
D=defoliation;
E=emergence inhibition;
G=growth retardation;
H=formative effects;
S=albinism;
U=unusual pigmentation;
6F=delayed flowering; and
6Y=flowerbuds abscised.

Compound 1
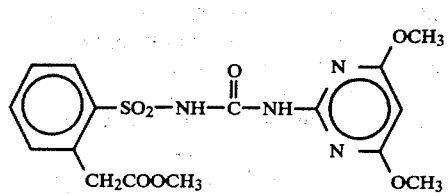

Compound 2
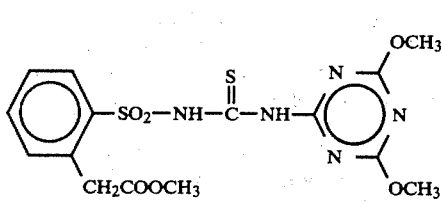

Compound 3
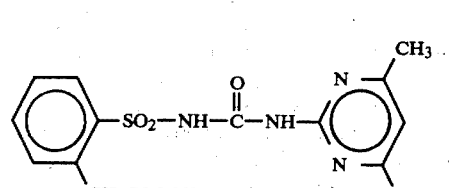

-continued

Compound 4
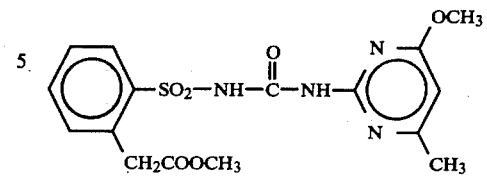

Compound 5
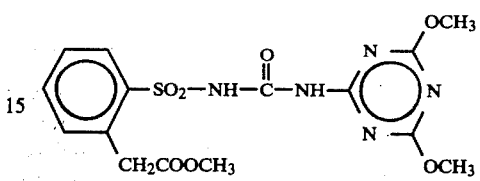

Compound 6
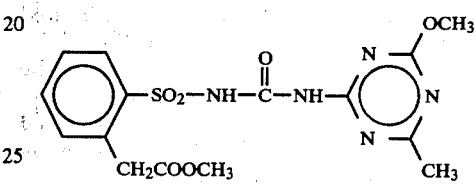

Compound 7
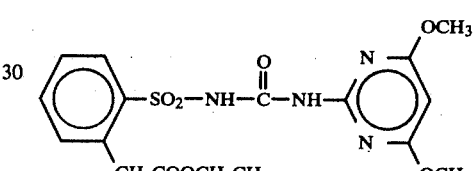

Compound 8
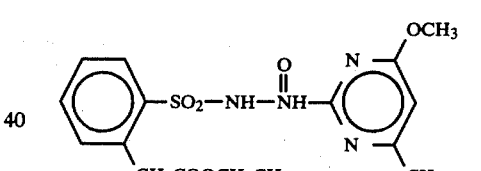

Compound 9
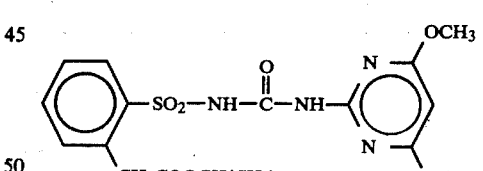

Compound 10
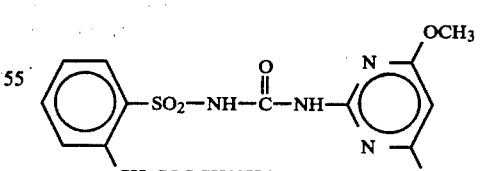

Compound 11
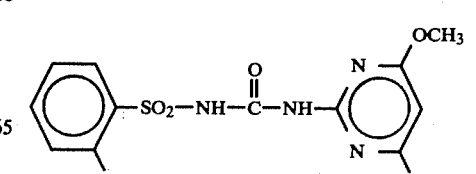

-continued

Compound 12
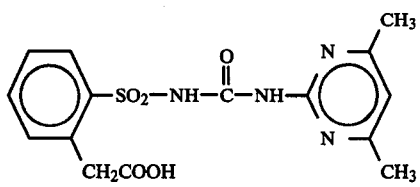

Compound 13
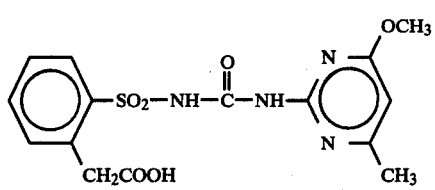

Compound 14
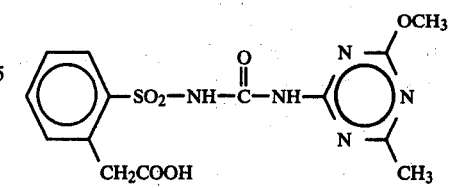

Compound 15
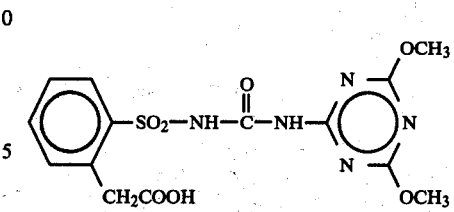

TABLE A

| | Compound 1 | Compound 2 | Compound 3 | Compound 4 | Compound 5 | Compound 6 | Compound 7 | Compound 8 |
|---|---|---|---|---|---|---|---|---|
| Rate kg/ha | .05 | 0.4 | 0.4 | 0.4 | .05 | .05 | 0.4 | 0.4 |
| POST-EMERGENCE | | | | | | | | |
| Bush bean | 9C | 9C | 9D,9G,6Y | 9D,9G,6Y | 9D,9G,6Y | 9C | 7C,9G | 6C,9G |
| Cotton | 5C,9G | 3C,9G | 2U,6C,9G | 10C | 4C,9G | 5C,9G | 5C,9G | 5C,9G |
| Morningglory | 3C,8H | 9C | 5C,9G | 9C | 9C | 10C | 3C,8H | 9C |
| Cocklebur | 5C,9H | 9C | 5C,9G | 5C,9H | 9C | 10C | 9C | 9C |
| Cassia | 6C,9G | 3C,7G | 2C,6G | 5C,9G | 3C,5G | 5C,9G | 9C | 5C,8G |
| Nutsedge | 3C,9G | 1C | 9G | 3C,9G | 0 | 0 | 2C,8G | 7G |
| Crabgrass | 4G | 0 | 10C | 9C | 1C | 0 | 2C | 2C,5G |
| Barnyardgrass | 4G | 1C,2H | 3C,9H | 9C | 1C | 1C | 2C,5H | 3C,9H |
| Wild Oats | 0 | 0 | 6C,9G | 5C,9G | 0 | 0 | 1C | 2C,5G |
| Wheat | 0 | 0 | 9C | 6C,9G | 0 | 0 | 0 | 1C,5G |
| Corn | 2C,8H | 0 | 1C,9G | 5U,9G | 1C | 2C,5H | 2C,6H | 2U,9G |
| Soybean | 2C,9G | 10C | 2C,8G | 9C | 5C,8G | 5C,9G | 6C,9G | 6C,9G |
| Rice | 5C,9G | 2G | 4C,9G | 9C | 1C,4G | 1C,6G | 3C,8G | 5C,9G |
| Sorghum | 9G | 3G | 9C | 5U,9C | 0 | 1C,6G | 2C,8H | 2C,8G |

| | Compound 9 | Compound 10 | Compound 11 | Compound 12 | Compound 13 | Compound 14 | Compound 15 |
|---|---|---|---|---|---|---|---|
| Rate kg/ha | .05 | 0.4 | 0.4 | 0.4 | 0.4 | 0.4 | 0.4 |
| POST-EMERGENCE | | | | | | | |
| Bush bean | 1C,6Y | 4C,7G,6Y | 9C | 2H,6F | 4C,7G,6Y | 9C | 4S,5G,6Y |
| Cotton | 2C | 2C,2H | 4C,8G | 1H | 2C,3H | 5C,9G | 4C,7G |
| Morningglory | 3B,8G | 0 | 1C | 0 | 1C | 9C | 2C,5G |
| Cocklebur | 3C,6G | 2C,6G | 3C,9G | 0 | 1C | 10C | 2C |
| Cassia | 2C | 2C | 3C,5G | 0 | 3C | 4C,8G | 2C |
| Nutsedge | 1C | 0 | 4G | 0 | 0 | 3G | 0 |
| Crabgrass | 0 | 0 | 2C | 0 | 2C | 1C | 0 |
| Barnyardgrass | 0 | 0 | 1C,5G | 1C | 3C,7H | 2C,6H | 0 |
| Wild Oats | 0 | 0 | 0 | 0 | 3G | 0 | 0 |
| Wheat | 0 | 0 | 0 | 0 | 2G | 0 | 0 |
| Corn | 0 | 0 | 1C | 0 | 2C,6H | 2C,9H | 0 |
| Soybean | 1C | 0 | 1C,3H | 0 | 3C,5G | 9C | 2C |
| Rice | 0 | 2G | 5G | 2C | 2C,6G | 1C,3G | 0 |
| Sorghum | 1C | 1C | 1C,5H | 1C | 2C,7H | 2C,5G | 0 |

| | Compound 1 | Compound 2 | Compound 3 | Compound 4 | Compound 5 | Compound 6 | Compound 7 | Compound 8 |
|---|---|---|---|---|---|---|---|---|
| Rate kg/ha | 0.5 | 0.4 | 0.4 | 0.4 | 0.5 | 0.5 | 0.4 | 0.4 |
| PRE-EMERGENCE | | | | | | | | |
| Morningglory | 9G | 9G | 5C,9G | 9C,9G | 9G | 5C,9G | 7G | 9G |
| Cocklebur | 9H | 9H | 9H | 9H | 9H | 9H | 9H | 9H |
| Cassia | 8G | 8G | 9G | 1C,9G | 8G | 3C,8G | 2C,8G | 8G |
| Nutsedge | 10E | 2G | 10E | 10E | 8G | 10E | 10E | 10E |
| Crabgrass | 5G | 1C | 1C,7G | 2C,9G | 3G | 2G | 1C | 3G |
| Barnyardgrass | 3C,5G | 3C | 2C,9H | 3C,9H | 1C | 1C | 2C,6H | 2C,8H |
| Wild Oats | 6G | 0 | 5C,9H | 3C,9H | 0 | 1C | 3G | 8G |
| Wheat | 5G | 0 | 9H | 9H | 0 | 2G | 0 | 8G |
| Corn | 8G | 7G | 9H | 10H | 1C,6G | 1C,8G | 2C,8G | 2C,9G |
| Soybean | 1H | 7H | 8H | 8H | 2C,3H | 2C,5H | 0 | 1C,3H |
| Rice | 10E | 9H | 10E | 10E | 5G | 1C,7G | 10E | 10E |
| Sorghum | 9G | 6G | 10H | 5C,9H | C,4G | 2C,9H | 2C,9H | 5C,9H |

| | Compound 9 | Compound 10 | Compound 11 | Compound 12 | Compound 13 | Compound 14 | Compound 15 |
|---|---|---|---|---|---|---|---|
| Rate kg/ha | .05 | 0.4 | 0.4 | 0.4 | 0.4 | 0.4 | 0.4 |

TABLE A-continued

PRE-EMERGENCE

| | | | | | | | |
|---|---|---|---|---|---|---|---|
| Morningglory | 2C,5G | 0 | 6G | 0 | 8G | 9G | 5G |
| Cocklebur | 2C,5G | 5H | 8H | 0 | 5H | 9H | 0 |
| Cassia | 1C | 4G | 2C,5G | 0 | 5G | 5C,8G | 0 |
| Nutsedge | 10E | 0 | 9G | 0 | 3G | 8G | 10E |
| Crabgrass | 2G | 0 | 2C | 0 | 1C | 0 | 1C |
| Barnyardgrass | 2G | 2G | 3C | 1C | 2C,7H | 2G | 1C |
| Wild Oats | 0 | 0 | 1C | 0 | 8G | 0 | 0 |
| Wheat | 0 | 0 | 1C | 0 | 5G | 0 | 0 |
| Corn | 2C,2G | 2C,4G | 3C,6H | 0 | 2C,7G | 2C,6G | 1C |
| Soybean | 0 | 1C | 2C | 0 | 1C,1H | 2C,6H | 0 |
| Rice | 2C | 1C,5G | 9H | 0 | 2C,8G | 1C,3G | 0 |
| Sorghum | 2G | 4G | 2C,8H | 0 | 2C,8H | 2C,8H | 0 |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

Test C

The test chemicals, dissolved in a non-phytotoxic solvent, were applied in an overall spray to the foliage and surrounding soil of selected plant species. One day after treatment, plants were checked for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugarbeets, and mustard. All plants were sprayed approximately 14 days after planting. Additional plant species are sometimes added to this standard test in order to evaluate unusual selectivity.

TABLE B

PRE-EMERGENCE ON FALLSINGTON SILT LOAM

| | Compound 1 | | Compound 2 | Compound 3 | Compound 4 | | Compound 8 | |
|---|---|---|---|---|---|---|---|---|
| Rate kg/ha | 0.06 | 0.25 | 0.25 | 0.12 | 0.03 | 0.12 | 0.06 | 0.25 |
| Crabgrass | 0 | 0 | 0 | 0 | 0 | 2G | 0 | 3G |
| Barnyardgrass | 2G | 3G | 0 | 3G | 2G | 5G | 3G | 5G,3C |
| Sorghum | 7G,5H | 7G,5H | 2G | 0 | 3G,2H | 9G,5H | 8G,5H | 9G,5H |
| Wild Oats | 0 | 0 | 0 | 0 | 2G | 4G | 4G | 7G |
| Johnsongrass | 0 | 0 | 0 | 0 | 0 | 5G,3H | 5G,3H | 5G,5H |
| Dallisgrass | 0 | 0 | 0 | 0 | 0 | 3G | 3G | 0 |
| Giant foxtail | 0 | 3G | 0 | 0 | 0 | 3G | 3G,3H | 7G,3H |
| Ky. bluegrass | 0 | 4G | 0 | 0 | 0 | 2G | 4G | 7G,3H |
| Cheatgrass | 0 | 3G | 0 | 0 | 3G | 4G | 5G,3C | 7G,3C |
| Sugarbeets | 0 | 7G | 0 | 3G | 5G | 7G,3H | 8G,9C | 10C |
| Corn | 0 | 0 | 0 | 0 | 0 | 2G | 3G,2C | 6G,2H |
| Mustard | 7G,3C | 8G,6C | 5G | 4G | 8G,8C | 8G,8C | 9G,9C | 10C |
| Cocklebur | 5G | 7G,3H | 0 | 0 | 0 | 3G | 6G,3H | 9G,9C |
| Pigweed | 0 | 8G,8C | 3G | 3G | 7G | 8G | 5G,3C | 10C |
| Nutsedge | 4G | 8G | 0 | 0 | 0 | 0 | 7G | 8G |
| Cotton | 4G | 5G,3H | 0 | 0 | 3G | 5G,3H | 3H | 5H |
| Morningglory | 3G | 6G | 0 | 0 | 3G | 6G | 6G,5H | 6G,5H |
| Cassia | 0 | 5G | 3G | 4G | 4G | 4G | 4G | 7G |
| Teaweed | 0 | 0 | 3G | 0 | 0 | 3G | 2G | 5G |
| Velvetleaf | 3G | 6G,5H | 3G | 0 | 4G,3H | 6G,5H | 5G,3H | 7G,8C |
| Jimsonweed | 0 | 4G | 0 | 0 | 0 | 5G,5C | 6G,4C | 7G,7C |
| Soybean | 0 | 0 | 2G | 0 | 2G | 0 | 2G | 5G,3H |
| Rice | 4G | 5G | 0 | 0 | 4G | 6G | 7G,3H | 8G,5H |
| Wheat | 0 | 0 | 0 | 0 | 0 | 0 | 3G | 5G |

TABLE C

Over-the-Top Soil/Foliage Treatment

| | Compound 2 | |
|---|---|---|
| Rate kg/ha | 0.06 | 0.25 |
| Soybeans | 3G,1C | 6G,3C |
| Velvetleaf | 9G,4C | 10G,8C |
| Sesbania | 9G,3C | 10G,6C |
| Cassia | 10G,3C | 10G,8C |
| Cotton | 8G,3C | 9G,4C |
| Morningglory | 10G,4C | 10C |
| Alfalfa | 1C | 1C |
| Jimsonweed | 1C | 3G,1C |
| Cocklebur | 9G,3C | 10G,5C |
| Corn | 0 | 0 |
| Crabgrass | 0 | 0 |
| Rice | 5G | 5G |
| Nutsedge | 0 | 0 |
| Barnyardgrass | 0 | 0 |
| Wheat | 0 | 0 |
| Giant foxtail | 0 | 1G |
| Wild Oats | 0 | 1C |
| Sorghum | 0 | 0 |

Test D

A test sample of compound 2 was formulated and applied directly to the water of simulated paddies, three days after transplanting of rice. The paddies were maintained in a greenhouse, and plant response ratings were taken one week and four weeks after application.

| Rate, kg ai/ha | Rice 1 wk. | Rice 4 wks. | Barnyard-grass* 4 weeks | Water Chestnut* 4 weeks | Arrow-head* 4 weeks |
|---|---|---|---|---|---|
| 0.125 | 0 | 0 | 0 | 8G | 0 |
| 0.5 | 0 | 0 | 0 | 10C | 6G |

*Echinochloa sp., Eleocharis sp., and Sagittaria sp., respectively.

Reference to the table above indicates that rice tolerated the application of the test sample at 500 g ai/ha, whereas the important weed (in rice culture in some areas) water chestnut was completely controlled. Arrowhead, which also is an important weed in some rice culture areas, was partially controlled at the same application rate.

What is claimed is:

1. A compound selected from:

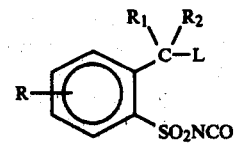

wherein
L is $CO_2R_{10}$;
R is H, F, Cl, Br, $NO_2$, $CF_3$, $C_1$–$C_3$ alkyl or $C_1$–$C_3$ alkoxy;
$R_1$ is H or $C_1$–$C_4$ alkyl;
$R_2$ is H or $CH_3$;
$R_{10}$ is $C_1$–$C_4$ alkyl, $C_3$–$C_4$ alkenyl, $CH_2CH_2Cl$ or $CH_2CH_2OCH_3$.

* * * * *